United States Patent [19]

Hildinger et al.

[11] Patent Number: 5,053,581
[45] Date of Patent: Oct. 1, 1991

[54] PROCESS FOR RECYCLING AND PURIFYING CONDENSATE FROM A HYDROCARBON OR ALCOHOL SYNTHESIS PROCESS

[75] Inventors: Henry W. Hildinger, Chester; Edwin D. Carlson, Sparta, both of N.J.

[73] Assignee: Exxon Research & Engineering Company, Florham Park, N.J.

[21] Appl. No.: 575,026

[22] Filed: Aug. 30, 1990

Related U.S. Application Data

[62] Division of Ser. No. 211,745, Jun. 27, 1988.

[51] Int. Cl.$^5$ .............................................. C07C 1/04
[52] U.S. Cl. .................................. 585/638; 585/733; 208/950; 518/715
[58] Field of Search ................. 208/950; 585/638, 733; 518/715

[56] References Cited

U.S. PATENT DOCUMENTS

| | | | |
|---|---|---|---|
| 4,298,695 | 11/1981 | Butter et al. | 208/950 |
| 4,579,985 | 4/1986 | Minderhound | 208/950 |
| 4,587,008 | 5/1986 | Minderhound | 518/715 |
| 4,640,766 | 2/1987 | Post et al. | 208/950 |
| 4,842,720 | 6/1989 | Moorehead | 518/950 |
| 4,962,078 | 10/1990 | Behrmann et al. | 518/715 |

Primary Examiner—Anthony McFarlane
Attorney, Agent, or Firm—Deborah L. Mellott

[57] ABSTRACT

This invention relates to a process of recycling condensate from a hydrocarbon or alcohol synthesis, wherein the condensate comprises water and contaminants such as lower molecular weight hydrocarbons, alcohols, and other oxygenates. A hot gaseous mixture comprising $CH_4$ and steam contacts the condensate so as to strip the contaminants from the condensate. The stripped contaminants, $CH_4$, and steam are separately recovered as a gaseous stream from the remaining purified water. The recovered $CH_4$-containing gaseous stream may be used in synthesis gas ($CO/H_2$) generation processes with the generated synthesis gas then being used in a hydrocarbon synthesis process to produce heavy hydrocarbons.

6 Claims, 1 Drawing Sheet

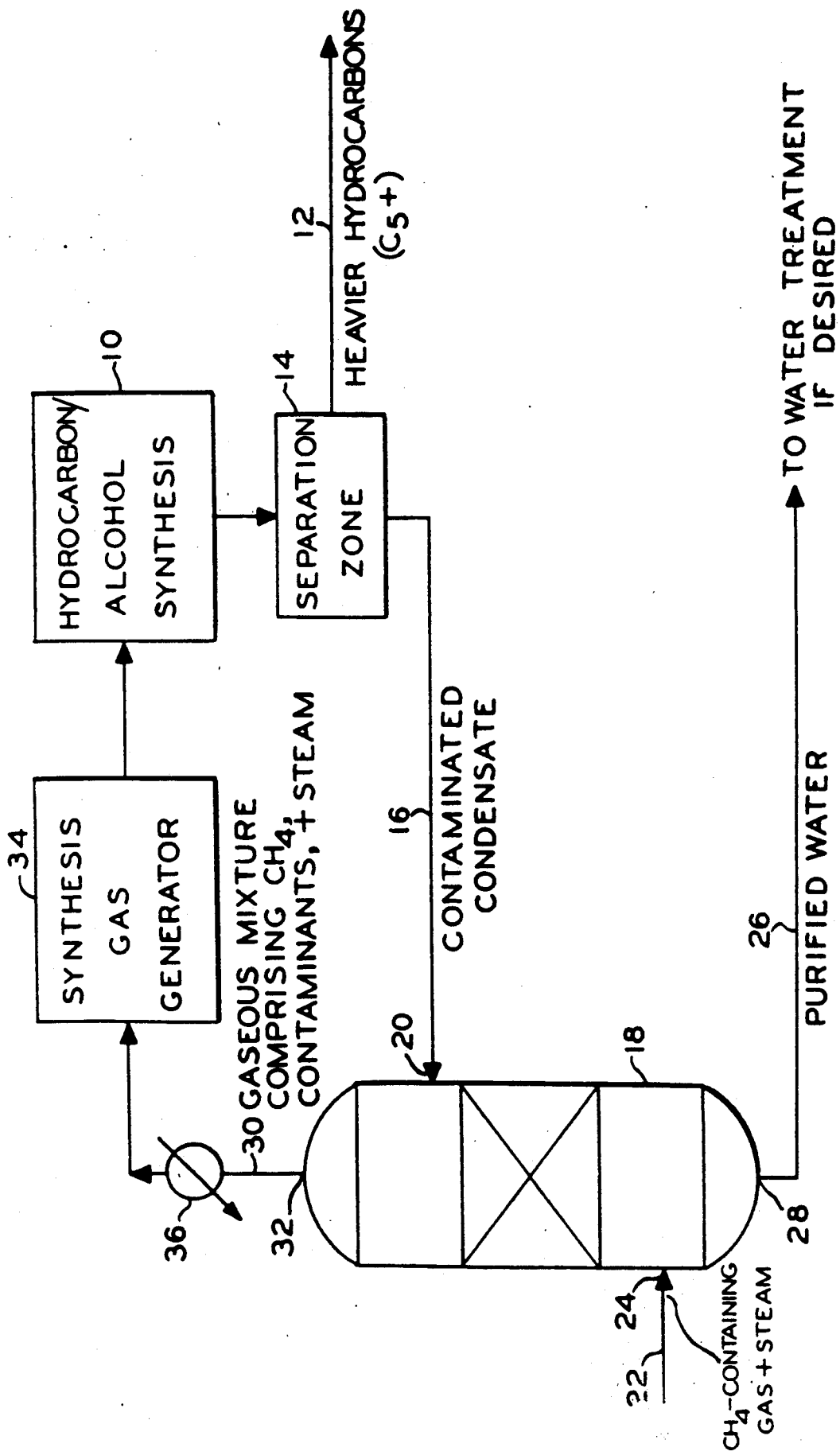

PROCESS FOR RECYCLING AND PURIFYING CONDENSATE FROM A HYDROCARBON OR ALCOHOL SYNTHESIS PROCESS

This is a division, of application Ser. No. 211,745, filed 6/27/88.

FIELD OF INVENTION

This invention relates to a process of recycling condensate from a hydrocarbon or alcohol synthesis, wherein the condensate comprises water and organic compounds such as oxygenates, alcohols, and hydrocarbons, which comprises contacting the condensate with a hot gaseous mixture, preferably comprising $CH_4$ and steam, to strip organic compounds and steam from the condensate; recovering a gaseous stream comprising the organic compounds; and separately recovering the purified liquid water of the condensate.

BACKGROUND OF THE INVENTION AND PRIOR ART

Carbon monoxide and hydrogen may be reacted over a suitable catalyst to produce hydrocarbons and oxygenated compounds (such as aldehydes and alcohols) containing one or more carbon atoms. Perhaps the best known of such processes is the Fischer-Tropsch process which involves the catalytic hydrogenation of carbon monoxide to produce a variety of products ranging in size and functionality from methane to higher alcohols. The methanation reaction was first described by Sabatier and Senderens in 1902. The later work of Fischer and Tropsch dealing with higher hydrocarbons was described in Brenstoff—Chem. 7, 97 (1926).

The product stream of a Fischer-Tropsch reaction or hydrocarbon synthesis will in general comprise hydrocarbon wax and a condensate. This condensate will typically comprise water and such compounds as hydrocarbons, alcohols, and other oxygenates; water being the predominate component. The desired heavy hydrocarbon product generally can be separated by sedimentation from the remaining liquid phase or condensate. The separation is not necessarily complete, though, and often the condensate will have present in it some of the lower molecular weight hydrocarbons and oxygenates in the liquid phase. This contaminated condensate is of little or no commercial value. The oxygenates are known to cause corrosion while the hydrocarbons may cause foaming. Thus, the condensate is normally passed to a water treatment facility where it undergoes typical water treatment steps, such as anaerobic digestion and biological oxidation, in order to remove the contaminants from the clean water.

It is known in the art to recycle the original condensate from a hydrocarbon synthesis or alcohol synthesis to a process where that condensate can be used as a supplemental reactant in the feedgas, thereby enriching the feedgas. European Patent Application No. 168892 discloses the recycling of organic products of a Fischer-Tropsch, methanol or oxo synthesis as a supplement to the feedgas to a steam reforming reaction. The recycled products increase the product yield and thermal efficiency of the steam reforming reaction.

The need exists in the art for a process of stripping the organic compounds or contaminants from the recycled condensate to produce a purified water stream, thereby eliminating the need for the complex and expensive water treatment processing while at the same time producing a stream of oxygenates, steam, and other organic compounds for use as a reactant in a feedgas to some other process, particularly a synthesis gas generation process.

SUMMARY OF THE INVENTION

The present invention is directed at the purification of a typical condensate stream from a hydrocarbon synthesis or alcohol synthesis process. The condensate typically comprises water and contaminants, such as lower molecular weight hydrocarbons (after the desired heavier hydrocarbons have been separated), alcohols, and other oxygenates; water being the predominate component. The condensate is contacted with a hot gaseous mixture comprising a light hydrocarbon gas, preferably comprising $CH_4$, and steam. The hot gaseous mixture strips the contaminants from the condensate leaving a stream of purified, clean water. The purified water has had about 80-90% of the contaminants removed. One advantage to this invention is that it provides an easy and cost saving process for purifying the condensate from synthesis processes without the need for expensive water treatment facilities.

In the above process, the contaminants are stripped from the condensate as a gaseous stream comprising lower molecular weight hydrocarbons; alcohols; other oxygenates; a light hydrocarbon gas, preferably comprising $CH_4$; and steam. Preferably, this light hydrocarbon gaseous stream, preferably $CH_4$-containing, is used as feedgas to a synthesis gas ($CO/H_2$) generation process or to any other process with suitable reactant requirements.

The invention also relates to a method of producing heavy hydrocarbons comprising reacting CO and $H_2$ over a catalyst at reaction conditions; separately recovering the heavy hydrocarbons from the condensate; contacting the condensate with a hot gaseous mixture preferably comprising $CH_4$ and steam to strip the condensate of any contaminants such as lower molecular weight hydrocarbons, alcohols, and other oxygenates; recovering a gaseous stream comprising the contaminants, $CH_4$, and steam; and converting the $CH_4$-containing stream to CO and $H_2$. Preferably, the $CH_4$-containing gaseous stream is converted to synthesis gas ($CO/H_2$) by a catalytic fluidized bed synthesis gas generation process or any combination of steam reforming and partial oxidation reactions with heat integration between the reactions. The CO and $H_2$ produced may then be used as feedgas in producing the heavy hydrocarbons.

BRIEF DESCRIPTION OF THE DRAWING

The FIGURE is a simplified schematic flow drawing of one method for practicing the subject invention.

DESCRIPTION OF THE PREFERRED EMBODIMENTS

The present invention provides a process of purifying a condensate stream from a hydrocarbon or alcohol synthesis process, thereby eliminating the need for expensive water treatment steps. In doing so, a hot gaseous stream comprising contaminants, $CH_4$, and steam is produced and used as feed gas to a synthesis gas generation process.

The condensate of the instant invention can come from a typical hydrocarbon synthesis process 10. The heavier hydrocarbons 12, preferably $C_5+$, are separated from the water phase or condensate by, for example, a sedimentation process 14. The remaining condensate 16, comprising predominately water and contaminants such as lower molecular weight hydrocarbons, alcohols, and other oxygenates, is passed to a vessel 18, preferably a sieved tray tower. A packed tower or any device that allows countercurrent vapor/liquid separation may also be used. The condensate enters the tower at or near the top at 20. A hot gaseous mixture comprising CH$_4$ and steam 22 is injected into the bottom of the tower at 24. The gaseous mixture is at a temperature in the range of about 450° F. to about 750° F. As the hot gaseous mixture contacts the downward flowing condensate, it causes the various contaminants and up to about fifty percent of the water present in the condensate to vaporize. The vaporized contaminants and steam rise to the top of the tower with the gaseous mixture comprising CH$_4$ and steam. The remaining fifty percent or so of the water in the condensate remains in liquid phase and having had most (about 80-90%) of the contaminants removed, is discharged as purified, clean water 26 at the bottom of the tower at 28. This purified water stream can then be passed to some reduced process of water treatment, if desired. However, the discharged stream is often sufficiently pure to meet environmental standards, and water treatment processing is not necessary.

The hot gaseous mixture 30 comprising CH$_4$, steam, and contaminants preferably exits the top of the vessel at 32 and is used in a synthesis gas (CO/H$_2$) generation process 34. This mixture must be hot, preferably at a temperature between about 750° F. to about 1200° F. upon entering the synthesis gas generation stage. The stream may be heated to the desired temperature by an external heating means 36, if necessary.

Synthesis gas can be produced by either steam reforming or partial oxidation. Conventionally, synthesis gas is produced by a mixture of steam reforming and partial oxidation reactions.

The steam reforming reaction is highly endothermic, produces a high ratio of hydrogen to carbon monoxide, and is described as:

$$CH_4 + H_2O \rightleftharpoons CO + 3H_2 \quad (1)$$

The partial oxidation reaction is highly exothermic, produces a low hydrogen to carbon monoxide ratio, and is described as:

$$CH_4 + O_2 \rightarrow CO + H_2 + H_2O \quad (2)$$

The combination of the two reactions is somewhat exothermic and is described as:

$$2CH_4 + O_2 \rightarrow 2CO + 4H_2$$

The combined process produces a 2:1 ratio of hydrogen to carbon monoxide.

Depending on the ratio of hydrogen to carbon monoxide desired in the synthesis gas product, the CH$_4$-containing gaseous stream 30 can be fed as feedgas separately to a steam reforming process or to a partial oxidation process, or to any combination of the two. The two reactions may take place in two separate vessels with or without a means of heat integration between them.

Preferably, the synthesis gas generation process involves the catalytic conversion of the CH$_4$-containing gas stream with oxygen and steam. More preferably, the catalytic conversion is effected in the presence of a fluidized bed of catalyst. Most preferably the catalyst is a nickel catalyst. The fluidized bed operates at an average temperature of about 1700° F. to 1900° F., preferably 1750° F., to 1850° F., and pressures of about 20 atm. to 40 atm.

A more preferred embodiment of this invention provides a process for producing heavy hydrocarbons, preferably C$_5$+ hydrocarbons. A feed gas of CO and H$_2$ is reacted over a suitable metal catalyst, for example an iron, cobalt, rhenium, or cobalt/rhenium catalyst supported on an inorganic refractory oxide, at normal synthesis conditions in a hydrocarbon or Fischer-Tropsch synthesis. Reaction temperatures for Fischer-Tropsch synthesis may vary over a range from about 320° F. to about 560° F., preferably about 350° F. to about 500° F. Reaction pressure may vary from about 80 psig to about 600 psig, preferably about 140 psig to about 400 psig. The gas feed rate, or gas hourly space velocity, in a Fischer-Tropsch reaction may vary from about 100 to about 5000 volume of fresh gas/volume of catalyst/hr. (V/V cat/hr.), preferably about 300 to about 2000 V/V cat/hr.

The product stream of the Fischer-Tropsch synthesis typically comprises C$_1$+ hydrocarbons and oxygenates (paraffins, olefins, aldehydes, alcohols, etc.) along with a contaminated water condensate. The composition of the product stream will vary depending upon the specific reaction conditions and catalysts used. In this invention a preferred product stream comprises heavy hydrocarbons, preferably C$_5$+ hydrocarbons. These heavier hydrocarbons may be separated from the contaminated water condensate by sedimentation or some other similar process. Some of the liquid lower molecular weight hydrocarbons remain in the condensate. The condensate typically comprises water and contaminants such as the lower molecular weight hydrocarbons, alcohols, and other oxygenates; water being the predominate component.

The contaminated condensate is passed to a vessel and contacted with a hot gaseous mixture comprising CH$_4$ and steam, as described previously, to strip the contaminants and about fifty percent of the water from the condensate leaving purified liquid water behind. The gaseous stream of contaminants, CH$_4$, and steam is recovered and converted to CO and H$_2$ via one of the synthesis gas generation processes previously described. The generated synthesis gas (CO/H$_2$) then may be fed to a hydrocarbon or Fischer-Tropsch synthesis to start again the entire process of producing heavy hydrocarbons, i.e., C$_5$+ hydrocarbons.

Having thus described the invention, it should be apparent that various modifications and changes can be made to the invention as claimed below without departing from the spirit of the invention.

What is claimed is:

1. A process for producing heavy hydrocarbons which comprises:

(a) reacting CO and H$_2$ over a catalyst at reactive conditions in a hydrocarbon synthesis to form heavy hydrocarbons and a product condensate;

(b) separately recovering the heavy hydrocarbons from the product condensate;

(c) contacting the product condensate with a hot gaseous mixture comprising CH$_4$ and steam to strip the product condensate of contaminants, said contaminants comprising lower molecular-weight hydrocarbons and oxygenates, (d) recovering a gaseous stream comprising the contaminants and the gaseous mixture; and
(e) converting the gaseous stream recovered in step (d) to CO and $H_2$ and utilizing at least a portion of said CO and $H_2$ in step (a).

2. The process of claim 1 wherein the gaseous stream of step (e) is converted to CO and $H_2$ by a process comprising reacting the gaseous stream with steam in a steam reforming reaction and with oxygen in a partial oxidation reaction.

3. The process of claim 1 wherein the gaseous stream of step (e) is converted to CO and $H_2$ by a process comprising the catalytic conversion of the gaseous stream with oxygen and steam.

4. The process of claim 3 wherein the catalytic conversion is effected with a fluidized bed of catalyst.

5. The process of claim 4 wherein the catalyst is a nickel catalyst.

6. The process of claim 1 wherein the heavy hydrocarbons are $C_5+$ hydrocarbons.

* * * * *